(12) United States Patent
Tonmukayakul et al.

(10) Patent No.: US 8,424,368 B2
(45) Date of Patent: Apr. 23, 2013

(54) METHOD FOR ESTIMATING PROPPANT TRANSPORT AND SUSPENDABILITY OF VISCOELASTIC LIQUIDS

(75) Inventors: Narongsak Tonmukayakul, Ducan, OK (US); Jeff F. Morris, Riverdale, NY (US); Robert Prudhomme, Lawrenceville, NJ (US)

(73) Assignee: Halliburton Energy Services, Inc., Houston, TX (US)

( * ) Notice: Subject to any disclaimer, the term of this patent is extended or adjusted under 35 U.S.C. 154(b) by 541 days.

(21) Appl. No.: 12/722,493

(22) Filed: Mar. 11, 2010

(65) Prior Publication Data
US 2011/0219856 A1   Sep. 15, 2011

(51) Int. Cl.
G01N 15/04 (2006.01)
(52) U.S. Cl.
USPC .................. 73/61.66; 73/61.65; 73/54.01
(58) Field of Classification Search .................. 73/61.65, 73/61.66
See application file for complete search history.

(56) References Cited

U.S. PATENT DOCUMENTS

| 6,782,735 | B2 | 8/2004 | Walters |
| 7,392,842 | B2 | 7/2008 | Morgan et al. |
| 2008/0190603 | A1 | 8/2008 | Brannon |
| 2010/0018294 | A1 | 1/2010 | Tonmukayakul |

OTHER PUBLICATIONS

Dimitris I. Collias & Robert K. Prud'homme, *Inhomogeneous Flows of Guar/Metal Ion Gels Observed by Laser Doppler Anemometry and Rheological Measurements*, J. Rheol. 38(2) 217-230 (1994).

Rosella Scirocco, Jan Vermant, & Jan Mewis, *Effect of the Viscoelasticity of the Suspending Fluid on Structure Formation in Suspensions*, J. Non-Newtonian Fluid Mech. 183-192 (2004).

Daejin Won & Chongyoup Kim, *Alignment and Aggregation of Spherical Particles in Viscoelastic Fluid under Shear Flow*, J. Non-Newtonian Fluid Mech. 141-146 (2003).

D.D. Joseph, Y.J. Liu, M. Poletto, & J. Feng, *Aggregation and Dispersion of Spheres Falling in Viscoelastic Liquids*, J. Non-Newtonian Fluid Mech. 45-86 (1994).

Ronald J. Phillips & Laurence Talini, *Chaining of Weakly Interacting Particles Suspended in Viscoelastic Fluids*, J. Non-Newtonian Fluid Mech. 175-188 (2007).

M.A. Tehrani, *An Experimental Study of Particle Migration in Pipe Flow of Viscoelastic Fluids*, J. Rheol. 40(6) 1057-1077 (1996).

M. K. Lyon, D. W. Mead, R. E. Elliot, & L.G. Leal, *Structure Formation in Moderately Concentrated Viscoelastic Suspensions in Simple Shear Flow*, J. Rheol. 45(4) 881-890 (2001).

Serge Bobroff & Ronald J Phillips, *Nuclear Magnetic Resonance Imaging Investigation of Sedimentation of Concentrated Suspensions in Non-Newtonian Fluids*, J. Rheol. 42(6) 1419-1436 (1998).

E. Allen, P.H.T. Uhlherr, *Nonhomogeneous Sedimentation in Viscoelastic Fluids*, J. Rheol. 33(4) 626-638 (1989).

S. Mora, L. Talini, & C. Allain, *Structuring Sedimentation in a Shear-Thinning Fluid*, Physical Review Letters 088301-1-4 (2005).

(Continued)

*Primary Examiner* — Hezron E Williams
*Assistant Examiner* — Paul West
(74) *Attorney, Agent, or Firm* — Robert A. Kent; McDermott Will & Emery LLP

(57) ABSTRACT

A method of determining one or more minimum rheological properties of a particle laden fluid is disclosed. The method includes determining one or more rheological properties of the fluid at a first shear rate, determining the settling velocity of the particles at the first shear rate, and obtaining a transport index for the fluid, the transport index indicating a relationship between the settling velocity and the one or more rheological properties.

20 Claims, 10 Drawing Sheets

OTHER PUBLICATIONS

H.A. Barnes, J. F. Hutton, & K. Walters, *An Introduction to Rheology* 1, 27-28 (Elsevier).

Raffi M. Turian, *Perturbation Solution of the Steady Newtonian Flow in the Cone and Plate and Parallel Plate Systems*, Ind. Eng. Chem. Fundam., vol. 11, No. 3, 361-368 (1972).

N. Adams & A. S. Lodge, *Philosophical Transactions of the Royal Society of London: Rheological Properties of Concentrated Polymer Solutions*, Royal Society, vol. 256, No. 1068, 149-184 (1964).

W.P. Cox, E.H. Merz, *Correlation of Dynamic and Steady Flow Viscosities*, J. Polymer Sci., vol. 28, No. 118, 619-622 (1958).

Brandon M. Baumert & Susan J. Muller, *Flow Visualization of the Elastic Taylor-Couette Instability in Boger Fluids*, Rheol. Acta. 34: 147-159 (1995).

Michael J. Economides, Larry T. Waters, & Shari Dunn-Norman, Petroleum Well Construction 490-493 (John Wiley & Sons 1998).

Peter Valko & Michael J. Economides, Hydraulic Fracture Mechanics 137-145 (Wiley 1995).

N. Tonmukayakul, J.E. Bryant, M.S. Talbot, & J.F. Morris, *Dynamic and Steady Shear Properties of Reversibly Cross-Linked Guar Solutions and Their Effects on Particle Settling Behavior*, New York, 3 pages.

N. Tonmukayakul, J.E. Bryant, M.S. Talbot, & J.F. Morris, *Sedimentation of Particles in Viscoelastic Fluids Under Imposed Shear Conditions*, New York, Jul. 30, 2009, pp. 1-7.

Phillip C. Harris, SPE, Harold Walers, *Real-Time Control of Low-Polymer Fracturing Fluids*, Texas, © 2000, pp. 1-9.

David F. James, *Boger Fluids*, Annual Rev. Fluid Mech., vol. 41, 129-142 (Jan. 2009).

B.H.A.A. van den Brule and G. Gheissary, *Effects of Fluid Elasticity on the Static and Dynamic Settling of a Spherical Particle*, Amsterdam, 1993, pp. 123-132.

Phillip C. Harris, Harold G. Walters, and Jason Bryant, *Prediction of Proppant Transport from Rheological Data*, Colorado, 2008, pp. 1-8.

Subramanian Kesavan and Robert K. Prud'homme, *Rheology of Guar and HPG Cross-Linked by Borate*, Princeton University, Princeton, New Jersey, 1992, pp. 2026-2032.

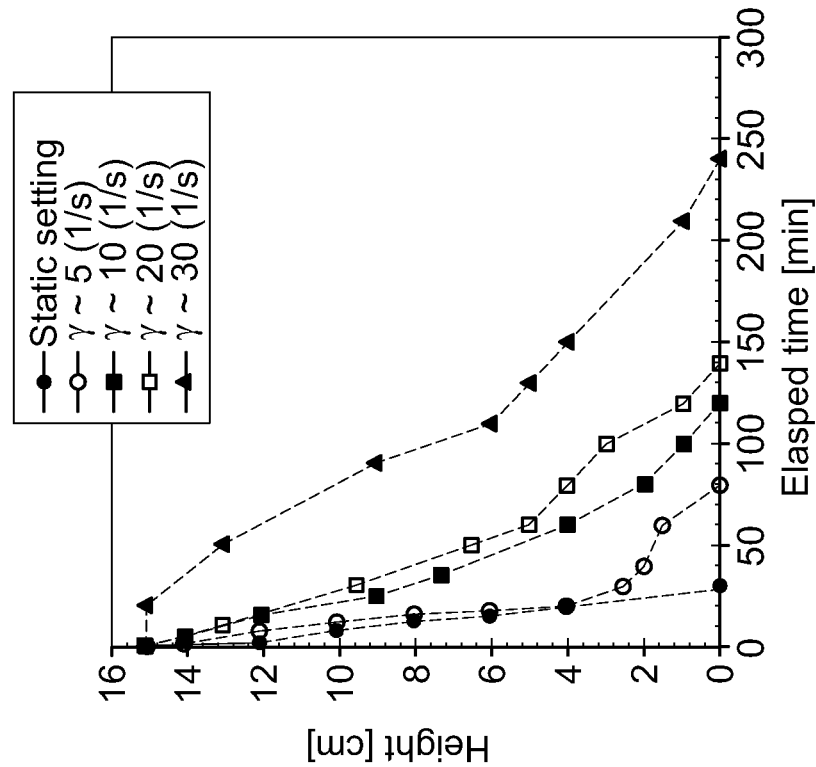
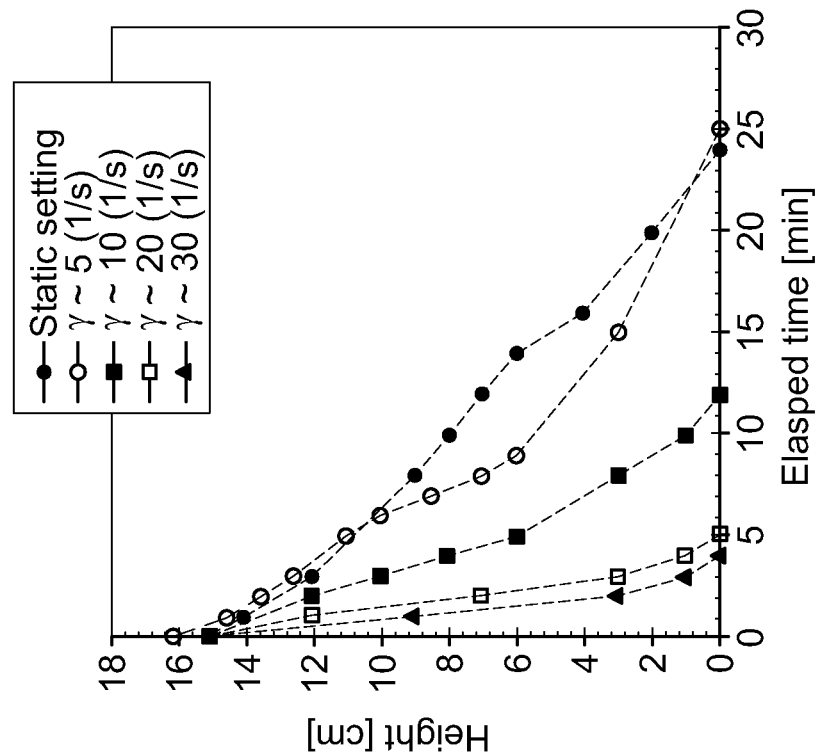
FIG. 6A
FIG. 6B

Sample A = Borate crosslinked guar with 31ppm borate ion
Sample B = Borate crosslinked guar with 125ppm borate ion
Sample C = 2%wt polmer in 5 times weight solvent
Sample D = 1%wt polmer in 5 times weight solvent
Sample E = 0.72%wt xanthan in 1%wt KCl solution
Sample F = 0.96%wt xanthan in 1%wt KCl solution

METHOD FOR ESTIMATING PROPPANT TRANSPORT AND SUSPENDABILITY OF VISCOELASTIC LIQUIDS

CROSS-REFERENCE TO RELATED APPLICATIONS

The subject matter of the present application is related to U.S. patent application Ser. No. 12/180,668, filed Jul. 28, 2008 and titled "Flow-Through Apparatus for Testing Particle Laden Fluids and methods of Making and Using Same," which is hereby incorporated herein by reference in its entirety for all purposes.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present disclosure generally relates to the field of rheometry. More specifically, this disclosure relates to a method for estimating proppant transport and the ability of viscoelastic fluids to suspend solid particles based on elastic properties during simple shear flow conditions.

BACKGROUND OF THE INVENTION

Sedimentation of solid particles is a basic phenomenon which impacts a wide range of applications and naturally-occurring phenomena. In fact, gravitationally-driven sedimentation and centrifugation are among the simplest and most widely-practiced techniques for liquid-solid separation, used for processes from industrial-scale water clarification to medical laboratory separation of blood components. As a consequence, sedimentation has a long history of study.

Settling in non-Newtonian fluids is of interest in a number of industrial contexts. Often, the goal is to minimize the sedimentation rate. For example, foodstuffs such as jams and yogurt are preferred to have uniform mixing of the solid fruit and seeds with the suspending continuous material. In cement and concrete, settling-induced separation of sand and aggregate particles from the cement paste is highly undesirable, and specialized transportation equipment, e.g., a rotating mixer truck, have been designed to maintain uniform mixing. In general, the methods available for minimizing settling are constrained by processing or end-product demands on the mixture (e.g., texture of a food product, flowability of concrete, etc.).

In hydraulic fracturing, large liquid pressure provided by pumps at the surface of the earth is used to pump a type of servicing fluid, referred to as a carrying fluid, through a wellbore into a subterranean zone at a rate and pressure such that fractures are formed or enhanced in a petroleum-bearing formation. It is to be understood that "subterranean formation" encompasses both areas below exposed earth and areas below earth covered by water such as ocean or fresh water. This is typically followed by the pumping of a carrying fluid having a slurry of solid particles (e.g., sand, an engineered material such as sintered bauxite or alumina, etc.) dispersed therein into the resulting fracture to hold or "prop" the fracture open when the fracturing pressure is removed and production of petroleum commences. The "proppant" particles then become deposited in the fracture and these particles function, inter alia, to hold the fracture open while maintaining conductive channels through which produced fluids may flow upon completion of the fracturing treatment and to release of the attendant hydraulic pressure.

The balance between flow properties and settling characteristics is central to hydraulic fracturing for petroleum well stimulation. For example, quality performance demands that the proppant be placed deep within the fracture, which requires that the excess weight of the solid proppant be supported during flow of the carrying fluid. It is desirable for the solid particles to be uniformly distributed for maximum effectiveness as a proppant and to minimize settling, which may be excessively rapid and detrimental to the process. In principle, settling rates can be reduced by increasing the viscosity of the slurry or carrying liquid, but this option is limited by the large distances under the surface at which the treatments are typically placed and the consequent large pressure drops associated with pumping. As a consequence, the liquids used for proppant slurries are typically viscoelastic polymeric solutions, gels, emulsions, or foams, with aqueous solutions of the naturally-occurring long-chain polymer guar being among the most common. To support the weight of proppants sufficiently well in many applications, it has been found that cross-linking (reversibly or irreversibly) of the guar solution results in an effective suspending medium without excessive viscosity to limit the pumpability of the liquid or slurries formed from it.

Rheology includes the study of the deformation and flow of matter. The rheology of reversible borate cross-linking of guar has been extensively studied. It has been found that shear history has less influence in reversibly cross-linked systems such as borate cross-linked guar than in permanently cross-linked systems, such as a zirconium cross-linked guar. In small-amplitude oscillatory measurements, reversibly cross-linked materials obey linear viscoelastic models, such as a Maxwell model. At high steady shear rates, reversibly cross-linked samples behave similarly to permanently cross-linked gels, which often break into domains and slip. Despite this knowledge, particle motion in reversibly cross-linked solutions under static settling and dynamic conditions is far from fully understood.

It is desirable to test particle-laden fluids or systems to determine if they are suitable for their intended use. However, in particle-laden fluids or suspensions, the particulate matter has a tendency to settle during an experiment, thereby often resulting in inaccurate measurements. Conventional rheometers do not take into account this settling effect in particle-laden fluids, nor do they maintain particle-laden fluids in suspension. Accordingly, reliable testing of the effect of particle settling on particle-laden fluids has been problematic due to the fact that existing rheometers have been unable to measure to a desired accuracy the rheological properties (e.g., viscosity) of a fluid having a high concentration of solids or particles.

Thus, it would be desirable to create methods of estimating proppant transport and the ability of non-Newtonian fluids to suspend particles, in order to assist in correlating base fluid rheology with particle settling, thereby allowing estimation of slurry transport efficiency and design of new fracturing fluid systems.

BRIEF DESCRIPTION OF THE DRAWINGS

The foregoing and other advantages of the invention will become apparent upon reading the following detailed description and upon reference to the drawings.

FIG. 6a shows the typical sedimentation behavior for the guar solution sample having a borate concentration of 31 ppm at various shear rates.

FIG. 6b shows the typical sedimentation behavior for the guar solution sample having a borate concentration of 93 ppm at various shear rates.

Figure 1:
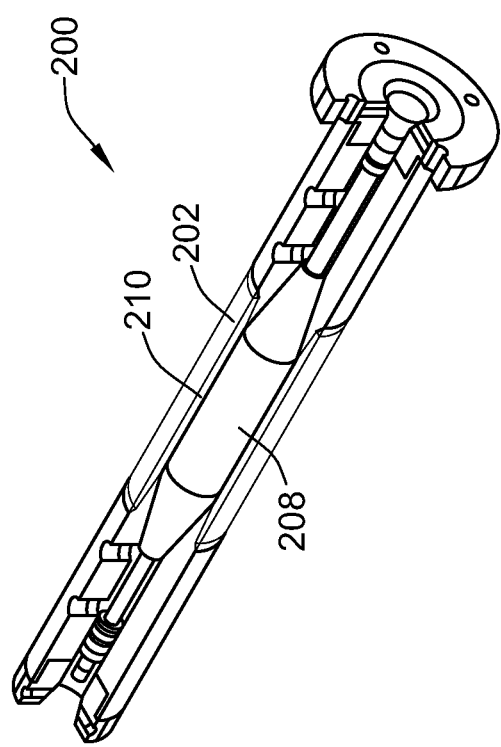
FIG. 1 illustrates a cross-sectional schematic of an embodiment of a flow-through apparatus.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION

It should be understood at the outset that although illustrative examples of one or more embodiments is provided below, the disclosed systems and/or methods may be implemented using any number of techniques, fluids, fluid components, or the like. The disclosure should in no way be limited to the illustrative implementations, drawings, and techniques illustrated below, including the exemplary methods and implementations illustrated and described herein, but may be modified within the scope of the appended claims along with their full scope of equivalents.

Rheological Data

As used herein, the term "rheometer" encompasses both multiple-speed testing and single-speed testing devices (the latter conventionally being referred to as a "viscometer" even if performed by the identical instrument capable of multiple-speed testing) for obtaining rheological properties of fluids.

The rheological properties of a borate cross-linked guar solution and constant viscosity high elasticity fluids (known as Boger fluids [REF]) were studied and compared using a transparent Couette cell device 200 with a fixed outer cylinder 202 and a rotating inner cylinder or bob 208, as shown in FIG. 1. The Couette cell device 200 was such that its cross-section could be imaged. The radius of the outer cylinder ($R_o$) 202 was about 36.12 mm, and the radius of the inner cylinder ($R_i$) was about 30.1 mm. Thus, the gap ratio of the flow-through apparatus ($\kappa = R_i/R_o$) equaled about 0.85, which is generally considered to be a narrow gap Couette cell. The immersed rotor length was about 161.2 mm. Rotation was driven by a servo motor (Danaher Motion, Radford, Va.). The settling profile was obtained from a standard CCD camera (resolution 1024×1000 pixels) captured at different time interval using a "homemade" particle-interface software that operates on MATLAB® software and the ImageJ image processing package. The one dimension settling velocity field ($v_{yz}$) of the settling interface was calculated by cross-correlating a corresponding intensity region in two successive images to determine the settling interface between the proppant and the cross-linked fluid. A variable speed pump fed sample into the Couette cell device 200 and, when desired, drove axial flow through a Couette gap 210 formed between the inner surface of the outer cylinder 202 and the outer surface of the inner cylinder 208. Descriptions of the flow-through device and the experimental procedure for gathering rheological data are provided in U.S. patent application Ser. No. 12/180,668, which is incorporated herein by reference in its entirety.

In the embodiments described herein, the rheological properties of borate cross-linked guar solution and constant viscosity high elasticity fluids were determined using a StressTech (Reologica Instruments AB, Sweden) controlled-stress rheometer, fitted with a cone-plate fixture.

To create the borate cross-linked guar solutions, about 6 grams of underivatized guar powder were added to about 2000 g of tap water. About 360 grams of nearly spherical particles having a density of about 3.7 g/cm$^3$ and particle sizes ranging from about 600 µm to about 700 µm were added, resulting in a viscoelastic suspension with solids occupying the fraction of about 0.02 of the total volume. The ratio of gap space to particle diameter ($R_o - R_i$)/d was greater than 10.

Separate viscoelastic solutions formed from guar solutions having added borate ion cross-linker concentrations of about 3 1 ppm, about 62 ppm, about 93 ppm, and about 125 ppm were used. The solutions were continuously mixed until the borate cross-linker was uniformly mixed. Each dispersion was then fed into the device where sedimentation experiments were conducted.

Selection criteria of the experimental fluids were based on the ability to differentiate the effects of elasticity, viscosity, and shear thinning on particle settling. The viscosity of the selected fluids was sufficiently high to yield sedimentation times over a distance of one centimeter in the range of minutes.

Figure 2B:
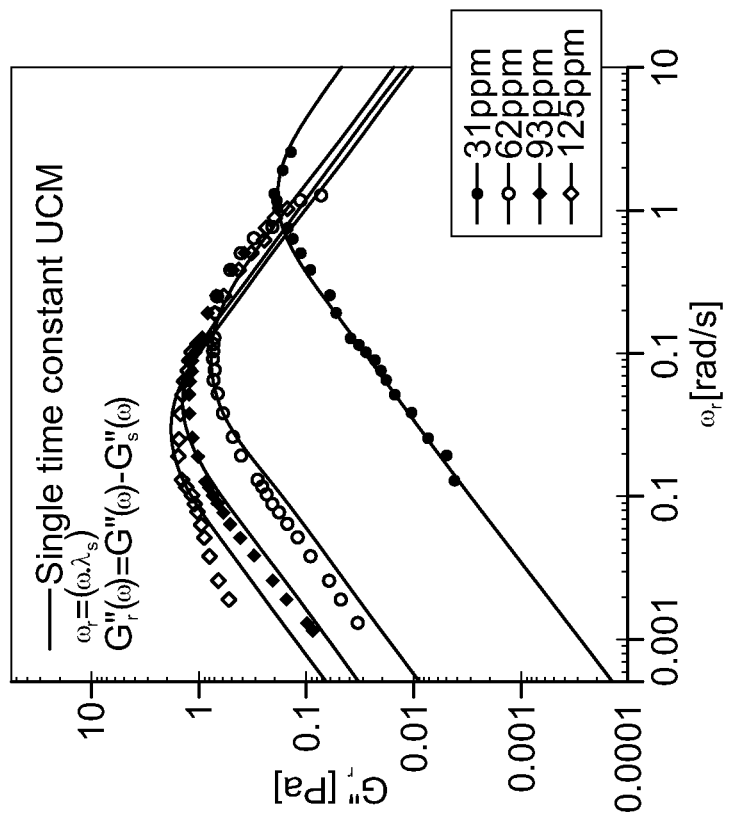
FIG. 2b is a graph of the loss moduli (G") of guar solution having borate ion concentrations of about 31 ppm, about 62 ppm, about 93 ppm, and about 125 ppm shown as a function of frequency of oscillation at a fixed stress of 1 Pa.
Figure 2A:
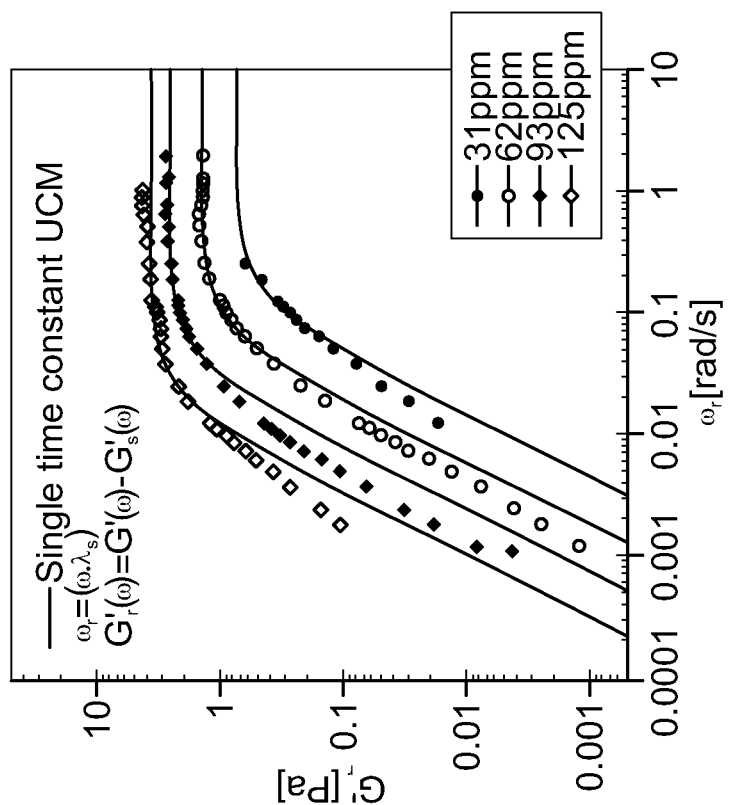
FIG. 2a is a graph of the storage moduli (G') of guar solution having borate ion concentrations of about 31 ppm, about 62 ppm, about 93 ppm, and about 125 ppm shown as a function of frequency of oscillation at a fixed stress of 1 Pa.

Storage moduli (G') and loss moduli (G") at cross-linker concentrations of 31 ppm, 62 ppm, 93 ppm, and 125 ppm are shown as a function of frequency in FIGS. 2a and 2b, respectively. The experimental results show two distinct trends of the moduli with respect to frequency. Solution-like behavior (G">G', indicating an entangled structure) is observed in the low-frequency range ($\omega$<0.01 rad/s), and gel-like behavior (G'>G", indicating a crosslinked network structure) is observed in the high-frequency range ($\omega$>0.01 rad/s).

In the high-frequency range, the storage modulus G' displays a characteristic plateau ($G'_p$) region. The $G'_p$ behavior is typical of a "strong gel" material that is observed when the characteristic relaxation time of the material is longer than the process time, that is, time per cycle of oscillation. The $G'_p$ behavior also indicates the intrinsic cross-linked network structure of the system. As shown in FIG. 2a, the magnitude of $G'_p$ increases dramatically to higher values with increasing cross-linker concentrations, indicating that the number of intermolecular association sites increases as the cross-linker concentration increases. The magnitude of $G'_p$ corresponds to the intrinsic "mesh size," or the average distance between the chain-to-chain cross-linking. Because the polymer concentration is generally constant in all samples, the cross-linker enhancing the network structure is assumed to be responsible for the increases in $G'_p$.

As shown in FIG. 2b, as frequency increases, the loss modulus G" increases noticeably from a local minimum value ($G''_{min}$) to a local maximum value ($G''_{max}$). Both $G''_{max}$ and $G''_{min}$ were measured at each cross-linker concentration within the tested frequency range. As the cross-linker concentration is increased, the G" response shifts to higher frequencies and $G''_{min}$ increases. The crossover frequency ($w_e$) where the values of the storage moduli G' and the loss moduli G" are equal and the crossover frequency can be used to provide quantitative information representing the relaxation time of the material.

FIG. 2b shows that $G''_{max}$ is relatively constant over the range of cross-linker concentration, while the value of $G''_{min}$ increases significantly with increasing cross-linker concentration. In the high-frequency range, the loss modulus G" shows a characteristic upturn from its minimum values $G''_{min}$ in the low-frequency range. This behavior may reflect a transition from the relaxation mechanism dominant at longer time-scales to a new relaxation mechanism dominant at shorter time-scales.

Figure 3:
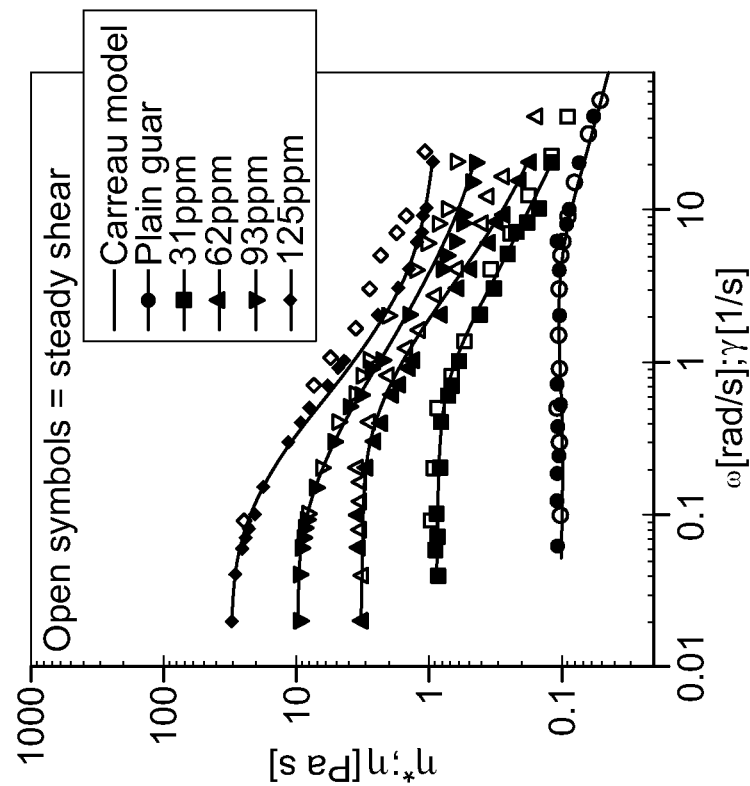
FIG. 3 illustrates the flow data of a borate cross-linked guar (0.3% wt guar) sample in terms of the complex viscosity ($\eta^*$) versus frequency ($\omega$) and shear rate ($\gamma$).

Referring to FIG. 3, flow data of the borate cross-linked guar (0.3% wt guar) is shown in terms of the complex viscosity ($\eta^*$, Pa.s) versus frequency ($\omega$, rad/s) and shear rate ($\gamma$, 1/s). Curve-fitting was performed using the Laverberg-Marquardt algorithm. FIG. 3 shows the dynamic, small-amplitude oscillatory shear (SAOS) viscosity and steady shear viscosity of borate cross-linked guar solutions having various cross-linker concentrations (0 ppm or plain guar, about 31 ppm, about 62 ppm, about 93 ppm, and about 125 ppm) at room temperature in the form of $\eta^*(\omega)$ and $\eta^*(\gamma)$ versus $\omega$ and $\gamma$. The steady shear viscosity values were plotted using open symbols (circle, square, triangles, diamond), and the dynamic shear viscosity (SAOS) values were plotted using closed (e.g., filled) symbols (circle, square, triangles, diamond). The magnitude of $\eta^*(\omega)$ was the same, within experimental uncertainty, as $\eta^*(\gamma)$ at equal values of $\omega$ and $\gamma$ for all samples. Good agreement between dynamic and steady shear viscosities was found for the 0 ppm (plain guar), 31 ppm, and 62 ppm samples, especially at $\omega, \gamma \leq 5_s^{-1}$. A reasonable agreement between dynamic and steady shear viscosities was observed for the 93 ppm and 125 ppm samples. Hence, the samples generally obeyed the Cox-Merz rule. Furthermore, $\eta^*(\omega)$ versus w can be satisfactorily described with a Carreau-Yasuda equation, and the results agree qualitatively with a single time Maxwell model. FIG. 3 also reveals that the initial viscosity $\eta_0^*$ increases with increasing borate ion concentration. Thus, it appears that shear thinning occurs at a smaller shear rate with increasing cross-linker concentration, implying an increased time scale for motion.

As further shown in FIG. 3, the samples display a narrower Newtonian range as cross-linker concentration increases. Increasing cross-linker concentration is expected to both increase the time scale of the interactions between the polymer chains and increase the number of intermolecular association sites, causing the intrinsic network to relax more slowly at high cross-linker concentrations. Slower relaxation thereby reduces the frequency-independent-viscosity range to lower frequencies.

Rheological data of the borate crosslinked guar samples obtained using dynamic shear and steady shear techniques is provided in Table 1 below

TABLE 1

Rheological Data of the Borate Cross-Linked Guar Samples

| | Plain guar | 31 ppm | 62 ppm | 93 ppm | 125 ppm |
| --- | --- | --- | --- | --- | --- |
| $\eta_0^*$ [Pa · s] | 0.1 | 0.89 | 3.21 | 9.96 | 32.56 |
| $\eta_\infty^*$ [Pa · s] | 0.03 | 0.045 | 0.08 | 0.25 | 0.98 |
| $\omega_S$ [rad/s] | 0.11 | 1.3 | 1.9 | 6.76 | 7.76 |
| n [—] | 0.3 | 0.37 | 0.5 | 0.54 | 0.68 |

$\omega_s$ in Table 1 above represents the critical frequency or deviation frequency where the fluid becomes non-Newtonian (i.e., the frequency at which $\eta$ is no longer constant). n in Table 1 above is the slope of the curve at frequencies above the given deviation frequencies.

Figure 4:
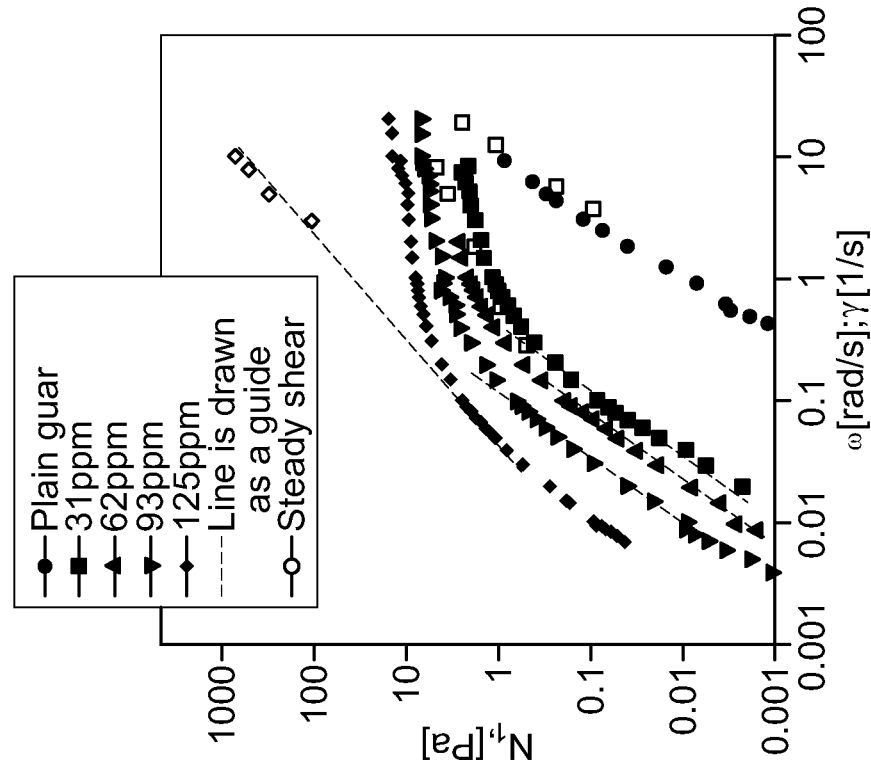
FIG. 4 shows the first normal stress difference ($N_1$) obtained from dynamic and steady shear measurements plotted as a function of frequency ($\omega$) and shear rate ($\gamma$).

Turning now to FIG. 4, the first normal stress difference $N_1$ is plotted as a function of frequency ($\omega$, rad/s) and shear rate ($\gamma$, 1/s). Using the Cox-Merz rule, the first normal stress difference $N_1$ can be estimated as $N_1 = \psi_1 \omega^2$, where $\psi_1$ is the first normal stress coefficient, which can be estimated as $\psi_1 = 2G'/\omega$, where G' is the storage modulus of the samples (see FIG. 2a). As discussed with respect to FIGS. 3a, 3b above, the steady shear values were plotted using closed symbols, while the dynamic shear values were plotted using open symbols.

FIG. 4 shows that the variation of the first normal stress difference $N_1$ versus $\omega$ and $\gamma$ increases generally linearly with $\gamma$ and $\omega$ before approaching its steady state at about $\omega \geq 1$ rad/s. This suggests that the network structure reaches its equilibrium state at the given amplitude and frequency. The difference in $N_1$ values obtained from the steady shear and the dynamic shear using the Cox-Merz rule were believed to be due to shear-induced rearrangement of the network junctions from "intra-junction" connections between points within a single guar polymer chain to "inter-junction" Connections between separate polymer chains. "Inter-junction" refers to association within the same polymer chain, while "intra-junction" refers to association between difference p[olymer chains. Namely, $N_1$ suggests when the inter-junction structure begins to have effects on the rheological behavior of the material. The measured $N_1$ was found to be asymptotic with the Cox-Merz data especially for $\gamma, \omega \leq 1s^{-1}$ rad/s, thereby indicating the practical capability of using the Cox-Merz rule as a tool for estimating $N_1$ of the borate ion guar system.

FIG. 4 also shows a comparison of $N_1$ values obtained from the SAOS (dynamic) and steady shear measurements. For the plain guar solution and guar-crosslinked at 31 ppm of borate ion, good agreement between the SAOS and steady shear data was observed for the whole shear rate and angular frequency range tested. For 125 ppm borate ion sample, a good agreement between the SAOS and steady shear data was observed at $\gamma \leq 10\,s^{-1}$, and vice versa for $\gamma \geq 10\,s^{-1}$. The evidence reveals explicitly a transition in the dynamic viscosity from solution-dominant to solvent-dominant values at $\gamma \geq 10\,s^{-1}$ region.

Measuring Settling Velocity Using a Flow-Through Device

Proppant settling velocity may be directly measured under a given shear condition using a developed flow-through device. The methods disclosed herein utilized a flow-through device as described in U.S. patent application Ser. No. 12/180,668, which is hereby incorporated by reference in its entirety. The system used with the embodiments of the present invention may also include at least one mixing vessel, at least one pump, and/or at least one computer system. In some embodiments, the system may further include at least one sample conditioning unit.

Figure 5:
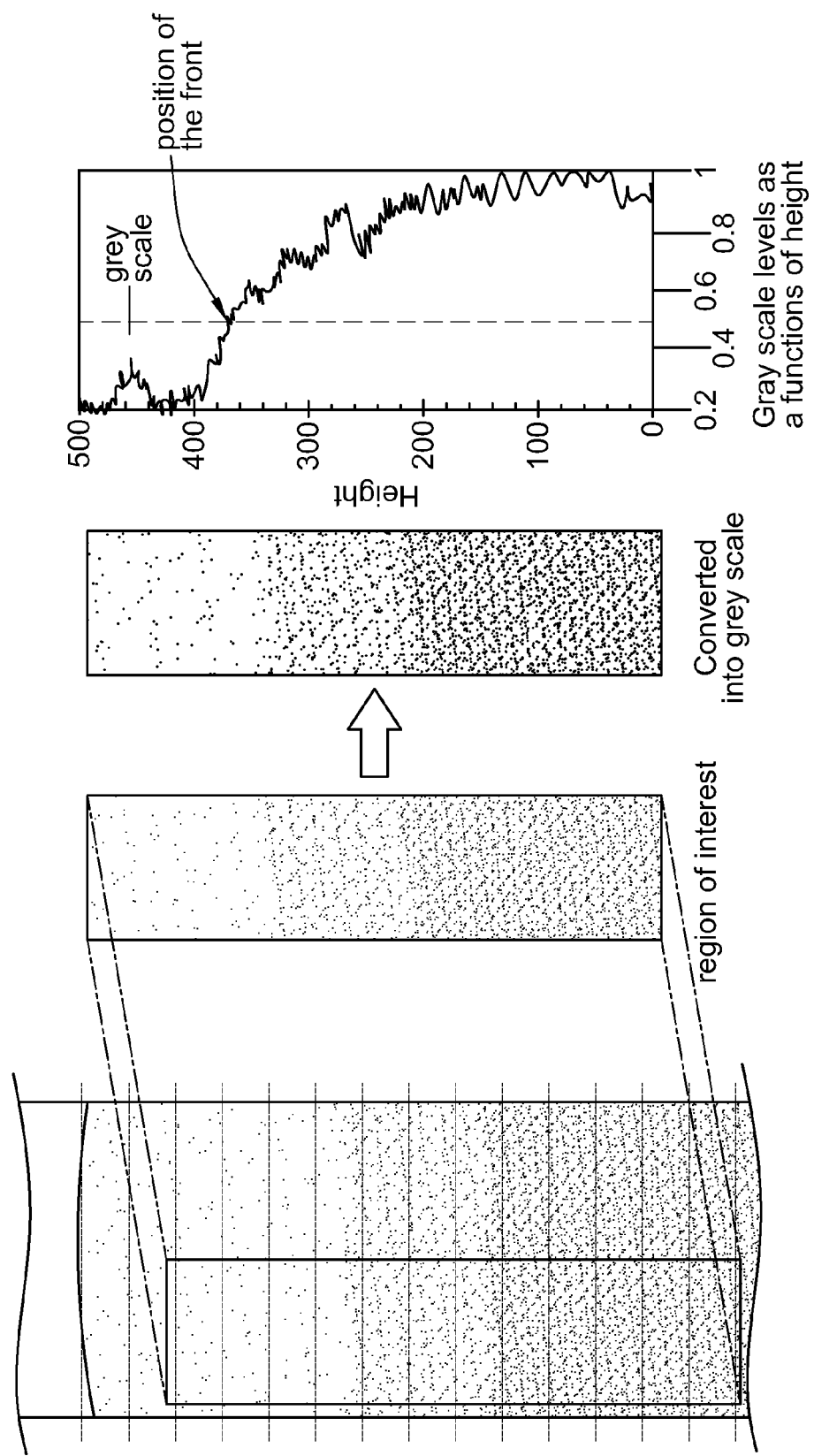
FIG. 5 illustrates the typical visualization method of a flow-through device used herein.

A visualization technique was used to capture the settling interface via a high resolution CCD camera equipped with software linked to systematically control the sequence and speed of the camera. A DC light source provided a constant light intensity onto the flow-through device. A simple numerical algorithm was used to convert picture pixel color level (light to dark scale) to 2D settling interface at a given time. FIG. 5 displays a typical visualization method used in this work.

Figure 6D:
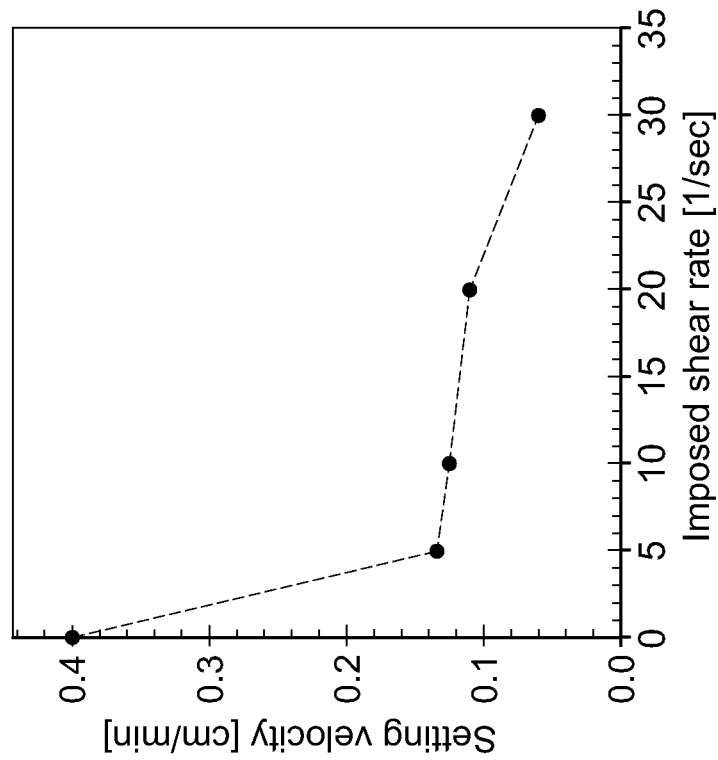
FIG. 6d illustrates the settling velocity as a function of imposed shear rate for the guar solution sample having a borate concentration of 93 ppm.

FIGS. 6a and 6b show the typical sedimentation behavior for the 31 ppm borate concentration (lightly elastic, viscosity dominant, faster relaxation time) sample and the 93 ppm (lightly viscous, elasticity dominant, slower relaxation time) sample, respectively, at imposed average shear rates of $0\,s^{-1}$, $5\,s^{-1}$, $10\,s^{-1}$, $20\,s^{-1}$ and $30\,s^{-1}$. The results are presented as settling height defined as the upper level of the particles above the bottom of the annular section of the device (in cm) versus time (in min). The settling velocity (in cm/min) is then determined as the slope of the settling height vs time data, and is plotted as a function of the imposed shear rate ($s^{-1}$) in FIGS. 6c, 6d for the 31 ppm borate concentration sample and the 93 ppm sample, respectively.

Figure 6C:
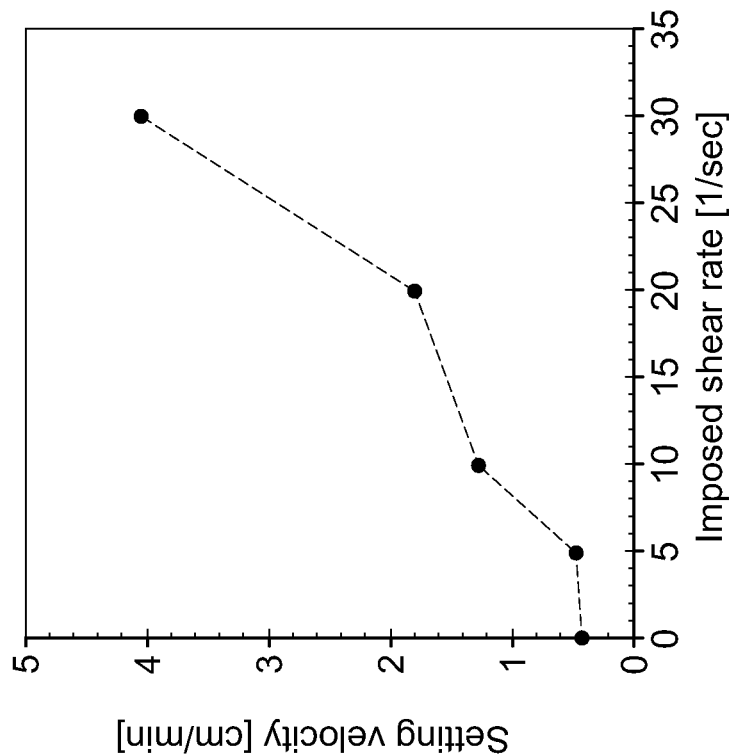
FIG. 6c illustrates the settling velocity as a function of imposed shear rate for the guar solution sample having a borate concentration of 31 ppm.

For the viscously-dominated sample (31 ppm borate), the particles were found to settle more rapidly with increasing shear rate (see FIGS. 6a, 6c). Under static conditions, the relaxation time was slower than the present time t, which caused the particles to settle more quickly. Under dynamic conditions, the relaxation time was also slower than t, and the polymer chains moved apart from each other due to shear. This caused inter-structure, alignment, and shear thinning, which also caused the particles to settle more quickly.

By contrast, the particles settled more gradually with increased shear rate for the elastically dominated sample (93 ppm) (see FIG. 6b, 6d). The 93 ppm sample was viscous-dominant at $\omega<10$ rad/s and was elastic-dominant at $\omega>10$ rad/s. As the particles settled, chain-like structures were formed. In static settling, the chain-like structures were in the vertical direction (parallel to gravity), and the relaxation time was slower than the present time t, which caused the particles to settle more quickly. For the dynamic settling, on the other hand, the chain-like structures were not yet ready to relax and were constrained by reptation (the back-and-forth motion of a polymer chain within its constraining space), which caused a tie intra-structure ellipsoidal shape. This increased the number of inter-structures, causing a normal force capable of better supporting proppant.

For the elastically dominated sample (93 ppm, FIGS. 6b, 6d), the elastic component dominated the gravitational force, and the particles stayed suspended in the liquid matrix for a longer period before the particles gradually settled in helical pattern. Particle migration, segregation, and alignment, caused by the combination of elastic and secondary flow, were all observed during the experiment. Taylor-Couette instability of viscoelastic fluids may also have played a role; this phenomenon results in a series of cellular vortical structures ("cells") each of which is in counter-rotation relative to the neighboring cell, resulting in an axial and radial component to the flow at all points in the annulus. This phenomenon is well-known to result from both inertia and elastic forces in the annular geometry, and here the conditions are appropriate for the elastic driving force but not inertia.

Proppant Transport Index

Also presented herein are the relationships between the settling velocity of particles and the dimensionless parameters governing fluid properties—the Deborah number (De) and the Weissenberg number (We). The Deborah number measures the degree of viscosity, or the relaxation time, of the network structure. The Weissenberg number measures the degree of elastic component. The Deborah number, a ratio of the polymer relaxation time to the characteristic flow time, can be estimated as De=$\lambda\omega$=$(\lambda\Omega_1 R_1)/(R_2-R_1)$. The Weissenberg number is herein defined as the ratio of a first normal stress difference to shear stress, We=$N_1/\sigma$, where $\sigma$ is the shear stress value. A simple physical model and scaling analysis based on this model are presented to explain the observation of normal stress influence on the settling.

A method developed according to the embodiments of the present invention may be used to determine the settling behavior and the relative distance of settling to axial motion in a fracturing application. This method employs the measurement or modeling of fluid rheology with no solid particles (as opposed to the mixture rheology, which includes solids) and the settling behavior of solid particles. The method is used to discriminate between the ability of different fluid formulations to carry solid particles under bounded flow (and hence shearing flow) conditions, as occurs in the pressure-driven flow along a fracture in hydraulic fracturing applications.

The method consists of defining a "proppant transport index (PTI)" and correlating this to the crucial material properties of the fluid. The transport of particles is characterized by the inverse of the fall speed, $V_s^{-1}$. A vanishing fall speed would imply that the proppant placement may be determined solely by the fluid motion of the mixture. Larger values of $V_s^{-1}$ imply better performance of the suspending fluid for particle transport purposes. A dimensionless form of the settling velocity may then be obtained by normalizing using the settling velocity in the absence of flow (V*) to its actual value $V_s$ so that PTI=$V^*/V_s$ may be considered.

For a dense particle in a flow of a viscoelastic fluid, the force balance in the direction of gravity involves the gravitational force ($F_{grav}$) balanced by a combination of a viscous force due to settling (first in the below equation) and an elastic force:

$$F_{vis}+F_{el}+F_{grav}=0 \qquad [1]$$

If we take a typical Stokes drag for the viscous term, and estimate the elastic force based on the magnitude of the normal stress difference, $N_1$, the balance [1] can then be written $$6\pi\eta(\dot\gamma)aV_s + 4\pi\alpha a^2|N_1(\dot\gamma)| - \frac{4\pi a^3}{3}\Delta\rho g = 0$$

with $\Delta\rho$ the excess density of the particle (sphere of radius a); here $\alpha$ is an O(1) parameter which is expected to be related to the strain induced by the weight of the particle but may be viewed as a fitting parameter. Solving for the settling velocity:

$$V_s = \frac{2a^2}{9\eta(\dot{\gamma})}\Delta\rho g - \frac{2a}{3}\frac{\alpha|N_1(\dot{\gamma})|}{\eta(\dot{\gamma})}$$

showing that the development of elastic stresses characterized by the normal stress difference may offset (due to the negative sign with all other terms defined positive, this reduces settling speed) the gravity effects, even when the viscosity drops.

This shows that a critical material parameter is the ratio $N_1/\eta$ at the shear rate conditions of interest. We can term the hypothetical velocity in the absence of elastic effects, at the actual viscosity $V_0$ and rewrite as $$V_s = V_0 - \frac{2a}{3}\frac{\alpha|N_1(\dot{\gamma})|}{\eta(\dot{\gamma})}$$

Recognizing that in the application of interest, the material is subjected to a shearing, an alternative form is $$V_s = V_0 - \frac{2\dot{\gamma}a}{3}\frac{\alpha|N_1(\dot{\gamma})|}{\eta(\dot{\gamma})\dot{\gamma}}$$

$$V_s = V_0 - \frac{2\dot{\gamma}a}{3}\alpha Wi$$

$$(We = |N_1|/\eta\dot{\gamma})$$

so that we see that if either if We (or $N_1/\eta$) increases the settling velocity will decrease, and PTI increases:

$$PTI = \frac{V^*}{V_s} = \frac{V^*}{\left[V_0 - \frac{2\dot{\gamma}a}{3}\alpha We\right]}$$

where $V^* = V_s(\dot{\gamma} = 0)$.

The first equality in the above equation shows that we must measure settling velocity, while the second illustrates how we may properly correlate the data to develop a predictive method.

Thus, for materials with finite settling velocity at zero shear rate:

If a material has PTI>1 at finite shear rate (or, if PTI=1/$V_s$ has a positive slope with respect to shear rate), the elastic normal stresses inhibit settling. This will happen if the growth of We with shear rate causes the last term in the bracket to grow faster than the first, i.e. faster than $V_0$ (the settling speed for a particle in a fluid with equivalent shear-rate dependent viscosity but no elasticity).

If a material has PTI<1 at finite shear rate (or if PTI=1/$V_s$ has a negative slope with respect to shear rate), then the shear thinning of the fluid dominates and, thus, the more rapid growth of $V_0$ dominates the elastic We term.

A Newtonian fluid has PTI=1, as it has no elasticity (We=0) and the viscosity is independent of shear rate: $V_0=V^*$ always.

Figure 11:
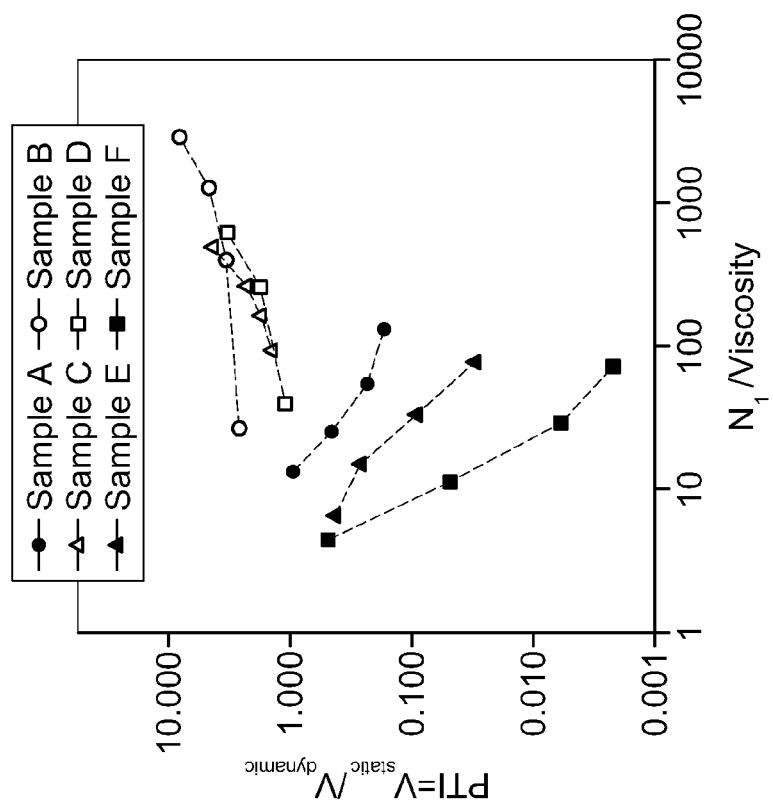
FIG. 11 plots $N_1$/viscosity versus the Proppant Transport Index (PTI) for various solutions.

The method entails 1) determining $V_s$ (by measuring the settling speed under shear at $\gamma$) and 2) determining We (or $N_1/\eta$) as a function of shear rate $\gamma$. The method allows the rapid assessment of the particle transport quality of a candidate non-Newtonian fluid. By determining the dependence of Vs as a function of We (or $N_1/\eta$), the PTI as defined above may be developed, and PTI>1 indicates a good quality fluid, while PTI<1 indicates a poor quality fluid. The method may thus be used to discriminate between two fluids as fracturing fluid candidates, as the variation of PTI with shear rate (at the temperature and other variables of interest) for the two fluids may be used to deduce the superior material for transport of the particles of interest. FIG. 11 plots $N_1$/viscosity versus the Proppant Transport Index (PTI) for various solutions.

The method may be used to predict the method may be used to predict the elastic transport characteristics of a fluid. This may be done without measurement of the settling velocity under shear. As shown by the analytical form of PTI equation above, a material which has an increasing PTI has elastic stresses which more effectively support particles even while its viscosity declines.

The method as outlined in the above provides a screening method for fracturing fluids. In application the reduced viscosity may make the material easier (less costly) to pump, while the ability to support solids is critical to proppant placement, so that an increasing PTI with shear rate may be indicative of a material which can satisfactorily place proppant while being sufficiently low viscosity to pump without excessive expense.

In summary, the correlation of PTI (or Vs) with We or $N_1/\eta$ allows prediction of the quality of proppant transport in a fracture job, and a prediction requiring only pure fluid rheology may be made based on the PTI equation above.

In an alternative embodiment, as above in all respects, the method may be applied with modeling of $N_1$ from linear viscoelastic (LVE) tests. Different expressions of the elastic force and viscous force may be employed. Those provided above are only examples (although other forms should only differ quantitatively and not qualitatively in the information one may deduce from them).

Figure 7:
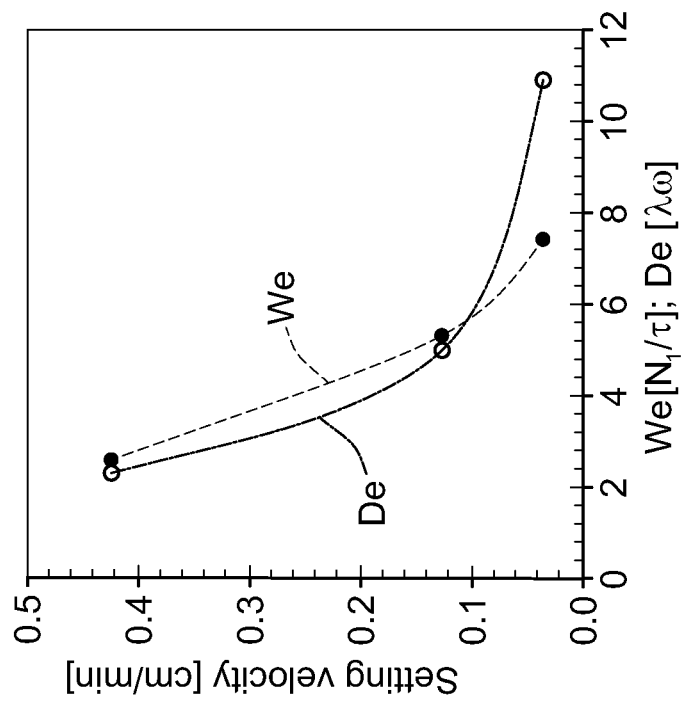
FIG. 7 is a graph of the settling velocity plotted as a function of the Weissenberg number (We) and the Deborah number (De) for guar solutions of concentration of 0.72% wt having borate concentrations of 31 ppm, 62 ppm, and 125 ppm.

Turning now to FIG. 7, settling velocity (cm/min) is plotted as a function of the Weissenberg number (We) and the Deborah number (De) for fluids having cross-linker concentrations of 31 ppm, 62 ppm, and 125 ppm (see Table 2 below).

TABLE 2

| Sample | Shear rate (1/s) | Shear stress (Pa) | Viscosity (Pa·s) | $N_1$ (Pa) | Wi ($N_1/\tau$) | Settling velocity (mm/s) | N1/viscosity | $V_0/V_s$ (PTI) |
|---|---|---|---|---|---|---|---|---|
| Borate crosslinked guar with 31 ppm Static Settling | 30.00 | 3.80 | 0.12 | 15.7 | 4.13 | 0.60 | 130.83 | 0.166 |
| | 20.0 | 3.01 | 0.15 | 8.21 | 2.72 | 0.43 | 54.56 | 0.23 |
| | 10 | 2.11 | 0.21 | 5.3 | 2.51 | 0.22 | 25.24 | 0.454 |
| | 5.0 | 1.42 | 0.28 | 3.7 | 2.61 | 0.11 | 13.21 | 0.94 |
| | | | | | | 0.1 | | 1 |
| Borate crosslinked guar with | 20.00 | 9.5 | 0.48 | 1371.0 | 144.32 | 0.01 | 2886.32 | 8 |
| | 10.02 | 6.09 | 0.61 | 774.0 | 127.05 | 0.02 | 1273.03 | 4.6 |
| | 8.00 | 5.41 | 0.68 | 576.3 | 106.56 | n.a | 852.51 | n.a |

TABLE 2-continued

| Sample | Shear rate (1/s) | Shear stress (Pa) | Viscosity (Pa·s) | $N_1$ (Pa) | Wi ($N_1/\tau$) | Settling velocity (mm/s) | N1/viscosity | $V_0/V_s$ (PTI) |
|---|---|---|---|---|---|---|---|---|
| 125 ppm | 5.0 | 4.33 | 0.87 | 342.0 | 79.12 | 0.03 | 395.61 | 3.3 |
|  | 3.0 | 13.65 | 4.55 | 120.6 | 8.83 | 0.03 | 26.50 | 2.6 |
| Static settling |  |  |  |  |  | 0.09 |  | 1 |
| 2% wt | 60 | 120.8 | 2.02 | 1270 | 10.51 |  |  |  |
| polymer in 5 | 50 | 100.2 | 2 | 973 | 9.71 | 0.09 | 486.50 | 4.28 |
| times by | 40 | 79.596 | 2.01 | 672 | 8.44 |  |  |  |
| weight of | 30 | 59.7 | 1.99 | 521 | 8.73 | 0.16 | 261.81 | 2.28 |
| corn | 20 | 40 | 2 | 326 | 8.13 | 0.22 | 163.00 | 1.71 |
| syrp + glycerol | 15 | 30.15 | 2.01 | 245 | 8.13 |  |  |  |
| mixture | 10 | 20.05 | 2.02 | 187 | 9.31 | 0.26 | 92.57 | 1.40 |
| Static Settling |  |  |  |  |  | 0.37 |  | 1 |
| 1% wt | 60 | 70.64 | 1.17 | 985.87 | 1395 | n.a | 837.38 |  |
| polymer in 5 | 50 | 59.145 | 1.1829 | 725.63 | 12.26 | 0.11 | 613.43 | 3.27 |
| times by | 40 | 47.475 | 1.186 | 498.67 | 10.50 | n.a | 420.15 |  |
| weight of | 30 | 35.88 | 1.196 | 307.46 | 8.56 | 0.205 | 257.07 | 1.756 |
| corn | 20 | 24.08 | 1.201 | 155.51 | 6.45 | n.a | 129.16 |  |
| syrp + glycerol | 15 | 18.27 | 1.208 | 95.88 | 5.24 | n.a | 78.72 |  |
| mixture | 10 | 12.272 | 1.22 | 48.501 | 3.95 | 0.33 | 39.52 | 1.09 |
| Static Settling |  |  |  |  |  | 0.36 |  | 1 |
| 0.72% wt of | 100 | 12.66 | 0.13 | 68.20 | 5.39 |  |  |  |
| xanthan + | 50.02 | 11.17 | 0.22 | 51.3 | 4.59 |  |  |  |
| 1% wt KCl | 20.0 | 9.55 | 0.48 | 36.8 | 3.85 | 0.86 | 77.05 | 0.03 |
|  | 10.02 | 8.47 | 0.85 | 27.8 | 3.28 | 0.32 | 32.88 | 0.09 |
|  | 5.0 | 7.41 | 1.48 | 22.0 | 2.97 | 0.11 | 14.85 | 0.26 |
|  | 3 | 6.27 | 2.41 | 15.67 | 2.61 | 0.07 | 6.49 | 0.42 |
|  | 1.38 | 6.01 | 4.55 | 10.52 | 1.68 |  |  |  |
| Static Settling |  |  |  |  |  | 0.03 |  | 1 |
| 0.96% wt of | 100 | 19.22 | 0.19 | 118.77 | 6.18 |  |  |  |
| xanthan + | 50.02 | 17.57 | 0.35 | 85.79 | 4.88 |  |  |  |
| 1% wt KCl | 20 | 15.60 | 0.78 | 55.74 | 3.57 | 0.45 | 71.45 | 0.0022 |
|  | 10.02 | 14.26 | 1.42 | 40.29 | 2.83 | 0.17 | 28.31 | 0.0059 |
|  | 5.0 | 13.03 | 2.60 | 29.07 | 2.23 | 0.03 | 11.16 | 0.048 |
|  | 3 | 11.90 | 4.78 | 20.94 | 1.76 | 0.017 | 4.38 | 0.48 |
|  | 1.38 | 11.03 | 8.0 | 15.86 | 1.44 | n/a |  |  |
| Static settling |  |  |  |  |  | 0.00102 |  | 1 |

As shown in FIG. 7, the Weissenberg number and the Deborah number generally have the same slope for cross-linker concentrations of 31 ppm to 62 ppm, thus indicating the same sensitivity over this range. Because both the Weissenberg number and the Deborah number are directly related to shear rate, the similarly of slopes at lower Weissenberg numbers and Deborah numbers indicates that when low stress and/or static conditions are applied, the network structure (viscosity) and elasticity contribute at equal order of magnitude to resisting the settling motion. The trend of elasticity and viscosity changing at generally the same rate is characteristic of Boger fluids (see below). However, as the shear rate increases (e.g., 62 ppm to 125 ppm) the Deborah number becomes constant sooner than the Weissenberg number. Thus, at static conditions, the structure (or viscosity) of a complex fluid has a significant effect on settling rate, as it depends more on the Deborah number. Under dynamic conditions, the elastic component plays a significant role on settling rate, as it depends more on the Weissenberg number (slope); thus, the elastic component, if a mechanism to generate elasticity is present, becomes dominant.

The Peclet number is defined by $Pe=(3\pi\eta_0 U_{sus} d^2)/(kT)$, where k is Boltzmann's constant and T is temperature. In this work, the Pe was larger than $10^{10}$. Hence, for these experimental conditions, hydrodynamic interactions are dominant over Brownian or colloidal effects on the settling particles, which may be considered negligible. Inertia as measured by the well-known Reynolds number $$\left(Re = \frac{|\Omega_2 - \Omega_1| R_1 (R_2 - R_1)}{(\eta/\rho)}\right).$$

is small and a more relevant Reynolds number based on the particle scale is negligibly small indicating inertia is of very small influence.

Comparison to Boger Fluids

The results obtained above were then compared to Boger fluids, in which viscosity is constant and elasticity changes, to determine which of viscosity or elasticity has a greater affect on settling velocity.

High viscosity Boger fluids were used. The Boger fluids were aqueous solutions of poly(AM-co-AA) (Sigma-Aldrich, St. Louis, Mo.) in a mixture of corn syrup (T. J. Blackburn Syrup Works, Inc., Jefferson, Tex.) and a glycerol solvent. The weight average molar mass of the polymer $M_w$ was about $5 \times 10^6$. The glycerol used was a commercial grade glycerin with about 99.7% purity grade having a density of about 1200 kg/m$^3$ (KIC Chemicals, Inc., New Paltz, N.Y.). The polymer samples were first dissolved in reverse osmosis (RO) purified water to give about 1% wt and about 2% wt solutions before being mixed with 5 folds weight of solvent. The ratio of corn syrup to glycerol in the solvent was about 7/3 (by weight). The resulting samples for rheological measurements were about 0.166% wt and 0.33% wt solutions of poly(AM-co-AA) in 7/3 (w/w) corn syrup/glycerol mixed solvent. About 360 grams of "proppant" particles having a density of 3.7 g/cm$^3$ and a particle size ranging from about 600 μm to about 700 μm and nearly spherical geometry were added, forming a viscoelastic suspension with the solid volume fraction of 0.02.

Figure 8B:
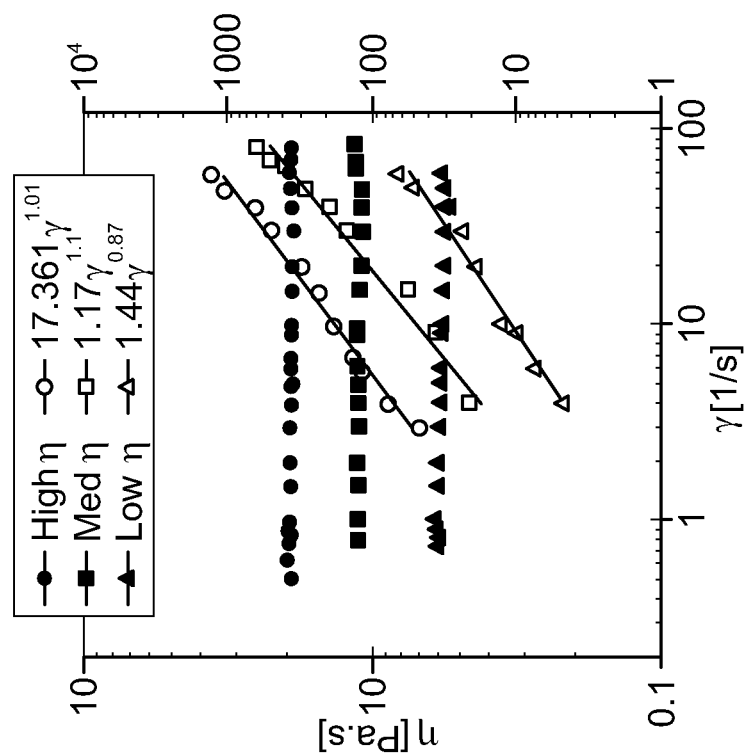
FIG. 8b is a graph of the steady shear viscosity ($\eta$) plotted as a function of shear rate ($\gamma$).
Figure 8A:
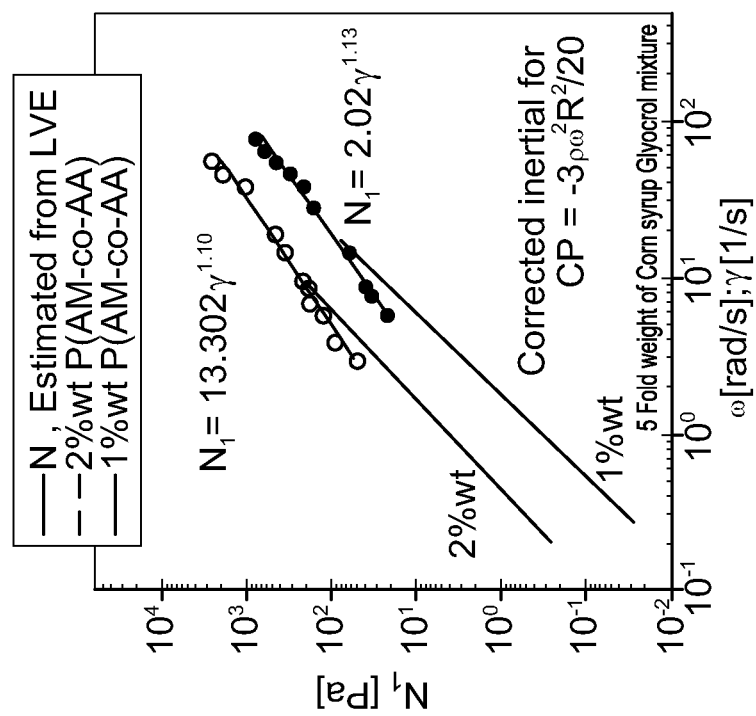
FIG. 8a is a graph of the first normal stress difference ($N_1$) plotted as a function of shear rate ($\gamma$).

Six constant viscosity high elasticity samples were used to determine roles of elasticity and viscosity on proppant particle settling rate under static and imposed shear conditions. The steady shear data are shown in FIGS. 8a, 8b where the steady shear viscosity (η) and the first normal stress difference ($N_1$) are plotted as a function of shear rate (γ) for samples having different polymer concentrations ("high," "medium," and "low"). Each fluid exhibited a constant viscosity η over the encompassing shear rate ranges found in a typical fracturing flow path both before and after testing, as expected of Boger fluids.

However, as shown in FIG. 8a, the first normal stress difference $N_1$ is not constant with shear, but increases with increasing shear rate. This increase in the first normal stress difference $N_1$ with increasing shear rate γ indicates that the degree of elasticity of the sample increases with increasing shear rate. Note that value of the measured first normal stress difference $N_1$ has been corrected for the inertial effect, $(N_1)_{inertia} = -3\rho\omega^2 R^2/20$, based on a Newtonian fluid, where ρ is the density of test fluid, ω is angular velocity of the equipment, and R is the radius of the measuring geometry.

The rheological behavior observed in FIG. 8b indicates that the materials satisfy the non-shear thinning criteria for being modeled by the Oldroyd-B constitutive equation. The quantity $\psi_1$ may be extracted using the Oldroyd-B model. $\psi_1$ is related to a relaxation time, λ, and is also related to the polymer viscosity contribution, $\eta_p$, as $\psi_1 = 2\lambda\eta_p$. Steady shear data were used to calculate a relaxation time denoted as $\lambda_s$ (see Table 3). The $\eta_p$ value was taken as the difference between the solution viscosity (η) and pure solvent viscosity ($\eta_s$). A second measure of the relaxation time was obtained through transient experiments. The decay of the first normal stress difference, $N_1 = \tau_{11} - \tau_{22}$, upon cessation of steady shear is exponential in the Oldroyd-B model. Transient relaxation times, $\lambda_t$, were obtained by fitting single exponentials to the measured decay rates of $N_1$. The difference between the relaxation times $\lambda_s$ and $\lambda_t$, is indicative of a broad spectrum of relaxation times for the Boger fluid solutions used in this work. Rheological properties of the constant viscosity, high elasticity fluids are given in Table 3 below.

TABLE 3

Rheological Data of Boger Fluids

| Sample no. | ρ (g/ml) | $\eta_s$ (Pa·s) | η (Pa·s) | $\lambda_s$ (s) | $\lambda_s$ (s) | El |
|---|---|---|---|---|---|---|
| 1 | 1.26 | 0.28 | 1.27 | 0.27 | 3.41 | 4.41 |
| 2 | 1.26 | 0.28 | 2.02 | 0.5 | 6.7 | 8.7 |
| 3 | 1.27 | 0.13 | 0.85 | 0.13 | 1.54 | 2.1 |
| 4 | 1.27 | 0.13 | 1.04 | 0.37 | 2.36 | 3.07 |
| 5 | 1.27 | 0.28 | 1.46 | 0.15 | 1.78 | 2.32 |
| 6 | 1.27 | 0.28 | 1.15 | 0.42 | 2.16 | 2.81 |

In Table 3, ρ is the density of the solution, $\eta_s$ is the viscosity of the solvent, η is the viscosity of the mixture, and $\lambda_s$ and $\lambda_s$ are measures of relaxation times. $\lambda_t$ is the transient decay of normal force, and $\lambda_s$ is calculated using the Oldroyd-B equation at steady shear.

El in Table 3 is the elasticity number defined as the ratio of the Deborah number (De=$\lambda_s\gamma$) to the Reynolds number $$\left(Re = \frac{|\Omega_2 - \Omega_1| R_1 (R_2 - R_1)}{(\eta/\rho)}\right).$$

In the Reynolds number, $\Omega_1$ and $\Omega_2$ are the rotational speeds of the two cylinders, and the Deborah number is defined as De=$(\lambda\Omega_1 R_1)/(R_2-R_1)$. The elasticity number (El) depends solely on fluid properties and geometric parameters and is, thus, defined as El=De/Re=$\eta\lambda/\rho(R_2-R_1)^2$.

Figure 9A:
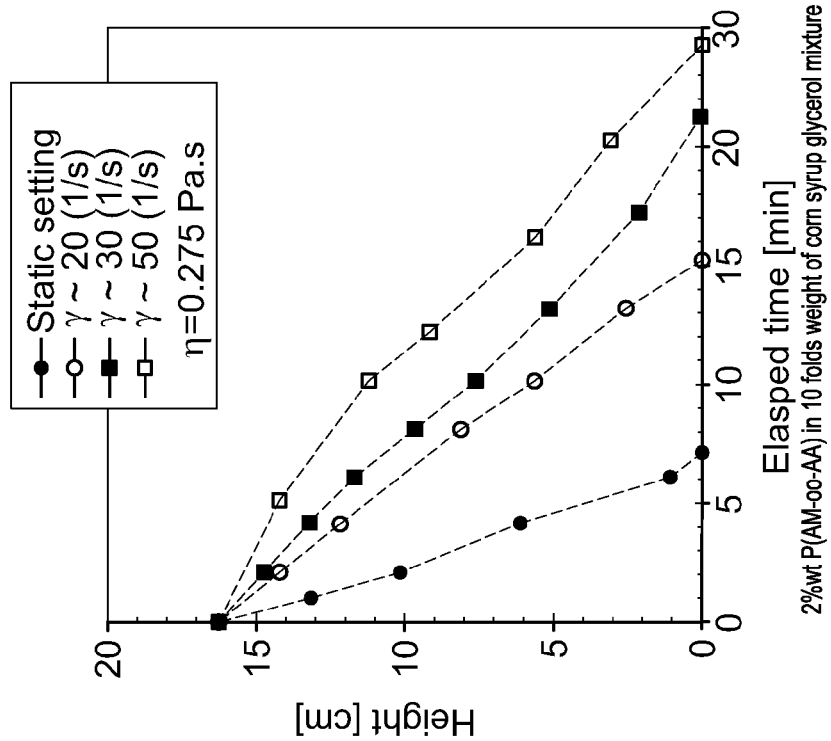
FIG. 9a plots height as a function of time for the 1% wt P(AM-co-AA) in 10 times by weight of corn syrup/glycerol mixture.
Figure 9B:
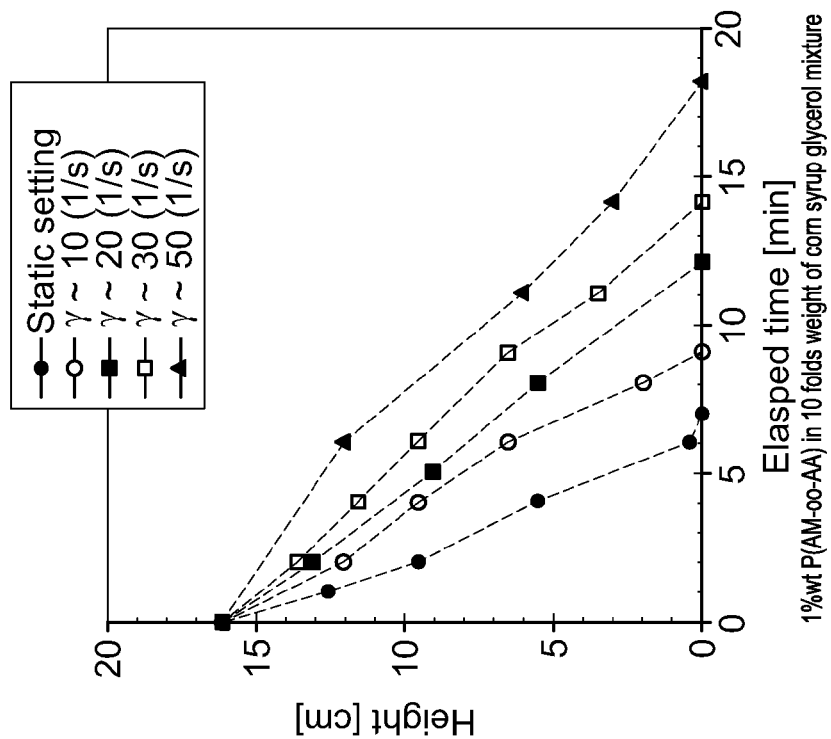
FIG. 9b plots height as a function of time for the 2% wt P(AM-co-AA) in 10 times by weight of corn syrup/glycerol mixture.

FIGS. 9a, 9b plot height (cm) of the suspended proppant as a function of time (min) for the Boger fluids for various shear rates γ. FIG. 9a includes data from 1% wt P(AM-co-AA) in 10 folds weight of corn syrup/glycerol mixture. FIG. 9b includes data from 2% wt P(AM-co-AA) in 10 folds weight of corn syrup/glycerol mixture. Although the viscosity of the two samples was generally the same, the 1% wt polymer has a generally lower degree of elasticity. As shown in FIGS. 9a, 9b, the time required for the proppant to settle under static conditions is generally the same for both the 1% wt polymer (FIG. 9a) and the 2% wt polymer (FIG. 9b). However, as shear rate increases, the settling time also increases. Furthermore, the settling time for the 2% wt polymer is greater than the settling time for the 1% wt polymer at the respective shear rates. As provided in FIG. 4 as discussed above, the degree of elastic component ($N_1$) increases with shear rate. Thus, from FIGS. 9a, 9b, it is evident that, as the degree of elasticity increases, the time required for the particles to settle also increases.

Results

Figure 10:
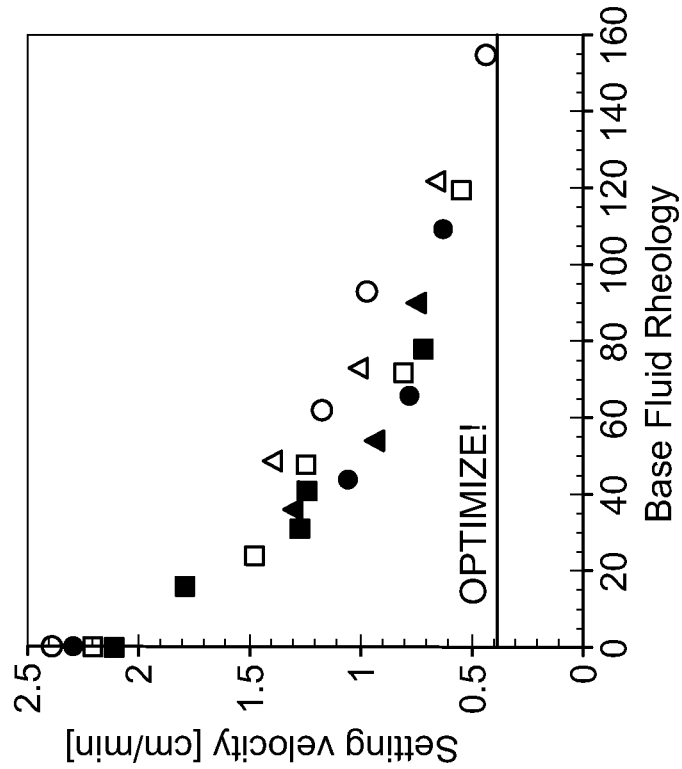
FIG. 10 illustrates settling velocity as a function of base fluid rheology.

FIG. 10 illustrates a graph of a proppant transport index, which plots settling velocity (cm/min) as a function of base fluid rheology (e.g., the Weissenberg number and/or the Deborah number). The proppant transport index is obtained by combining the information regarding (1) rheological information of carrying fluids (see FIG. 3) with (2) the settling characteristics obtained using the flow-through device (see FIG. 6b). The rheological information includes elasticity, viscosity, yield stress, and/or degree of shear thinning. The resulting proppant transport index shows the settling-rheology relationship of a particular fluid.

The key rheological parameters gathered from the testing described above may be used to optimize a hydraulic fracturing treatment. For example, fracture geometry is generally known from existing simulations. The shear rate may be calculated therefrom for a given pumping rate. Once it is decided which materials (proppant and carrying fluid) are to be used, $N_1$ may be obtained from taking the required rheological measurements. The Weissenberg number may then be obtained, and from that, the proppant settling velocity may be estimated. Alternatively, at a constant viscosity, the proppant transport index of FIG. 10 provides how much elastic component would be needed to obtain particle settling at a desired velocity.

The proppant transport index (PTI) may be used to quickly assess whether a fluid will have the ability to carry solid particles sufficiently well to work in a given application. For example, the PTI yields the time for settling a given distance, and the application engineer may consider the flow rate imposed to determine the time necessary to flow the resulting distance into a fracture where it is necessary to place proppant. If the PTI indicates that the settling is too large on this time (an engineering judgment based on acceptable performance for the application) then the materials to be used would need to be modified. Note that PTI is specific to the particle size and density considered.

The results presented herein reveal a remarkably strong reduction of settling by elasticity of the liquid, which is seen even for liquids which exhibit shear-thinning if the normal stress is found to grow sufficiently rapidly. A simple conceptual model allows the development of a scaling law which explains the observed dependence of settling velocity upon the Weissenberg number, defined as the ratio of the first normal stress difference to the shear stress, $We=N_1/\sigma$. A balance of forces shows how flow-induced elastic forces can support part of the weight of a particle and thus reduce the fall speed. This leads to the general conclusion that normal stresses in a viscoelastic fluid may have pronounced effects on the motions and distribution of solids within the fluid.

A simple analysis of the settling of a particle through a viscoelastic liquid undergoing an imposed shearing motion may also be performed. It is assumed that all motions are at low Reynolds numbers. For a particle settling in a viscoelastic liquid, the forces on the particle in the direction of gravity (taking the negative direction along gravity) are the driving excess weight $F_g = -(4\pi a^3/3)\Delta\rho g$, a viscous drag which may be written $F_d = -6\pi\eta aU$ where U is the settling velocity, and an elastic force, $F_e$, which is assumed to resist gravity. The elastic force is of unknown form, but may be expressed in terms of the liquid normal stress difference as $F_e = (4\pi a^2)\alpha N_1$ where $4\pi a^2$ is the particle surface area, $N_1$ is the liquid first normal stress difference, and $\alpha$ is an unknown but positive dimensionless coefficient. Assuming the particle to be spherical of radius a and in steady motion, the forces on the particle must balance, $F_g + F_d + F_e = 0$, which may be rewritten as $$-\frac{4\pi a^3}{3}\Delta\rho g + 6\pi\eta aU + 4\pi a^2 \alpha N_1 = 0$$

In a dynamic settling experiment, the liquid is subjected to a shear stress $\sigma$. Using this imposed stress and the particle surface area to provide a force scale of $4\pi a^2 \sigma$ we normalize all terms to arrive at $$-\frac{a}{3\sigma}\Delta\rho g + \frac{3}{2}\frac{\eta U}{\sigma a} + \alpha We = 0.$$

Here, the Weissenberg number is given by $We=N_1/\sigma$ and characterizes the ratio of shear-induced normal stresses to the imposed shear stress. Because $\eta$, U, and $\sigma=\eta\gamma$ are all rate-dependent, it is useful to replace the stress $\sigma$ in the second term to yield $$-\frac{a}{3\eta\dot\gamma}\Delta\rho g + \frac{3U}{2\dot\gamma} + \alpha We = 0$$

Noting that $\gamma$ increases at least proportionally to $\sigma$ and faster if the material shear thins, this form immediately provides a prediction of interest. At low rates, where $We \to 0$, the velocity is given by $$\text{small } We: \quad U \approx \frac{2a^2\Delta\rho g}{9\eta(\dot\gamma)}.$$

Note that this is a quasi-Newtonian form. The rate-dependence of the viscosity is included, and for fluids showing shear-thinning but negligible elasticity, the expectation is that U increases with increasing shear rate, in agreement with the settling behavior in a lightly cross-linked guar solution fluid of 31 ppm borate (see FIG. 6c).

For a fluid that exhibits normal stress differences, with We non-negligible, we find $$U = \frac{2a^2\Delta\rho g}{9\eta(\dot\gamma)} - \frac{2}{3}\dot\gamma a\alpha We.$$

Quite generally, we see that the final "elastic" term offsets the weight of the particle. As We increases, the fall speed U is predicted to decrease as a progressively larger fraction of the excess weight of the particle is balanced by the elastic normal stress exerted by the fluid. We interpret the physics behind this prediction as follows. A particle immersed in shear flow disturbs the streamlines The elastic stresses along the streamlines ($\sigma_{11}$ in $N_1=\sigma_{11}-\sigma_{22}$) are brought into play because a particle deflects the streamlines of constant stress, and there will be a resulting force opposing this deflection. Because a heavy particle generates a bias, owing to a larger deflection on the lower side of the particle, there is net elastic force up on the particle. The prediction is borne out by the data presented for a more heavily cross-linked guar sample (e.g., 93 ppm borate, see FIGS. 6b, 6d), and also for the Boger fluids studied here.

The results for the Boger fluids indicate that a cross-linked network is not essential, and that a simple force balance captures the idea. The Boger fluid is formed from a polymeric solution, without interchain crosslinking of the macromolecular chains, so that the elasticity is not dependent on a network formation, and can even be shown to result in a slowing of settling at levels of polymer too low to exhibit chain overlap (entanglement).

The results indicate that the settling characteristics for isolated particles as a function of rate may be deduced from a thorough but straightforward rheological characterization. It is not necessary to perform the difficult fluid mechanical calculations of particle motion in shear fields.

According to one process of the present invention, a method of determining one or more minimum rheological properties of a particle laden fluid includes determining one or more rheological properties of the fluid at a first shear rate, determining the settling velocity of the particles at the first shear rate, and obtaining a transport index for the fluid, the transport index indicating a relationship between the settling velocity and the one or more rheological properties.

According to another process, a method of determining proppant supportability of a carrying fluid including the proppant includes determining at least one rheological property of the carrying fluid, the at least one rheological property being associated with elasticity or viscosity, determining the settling velocity of the proppant under imposed shear conditions, and developing a proppant transport index indicating a relationship between the at least one rheological property and the settling velocity.

What is claimed is:
1. A method of determining one or more minimum rheological properties of a particle laden fluid, the method comprising the acts of:
   determining one or more rheological properties of the fluid at a first shear rate;
   determining the settling velocity of the particles at the first shear rate; and obtaining a transport index for the fluid, the transport index indicating a relationship between the settling velocity and the one or more rheological properties, wherein the settling velocity is determined using a flow-through device.

2. The method of claim 1, wherein the one or more rheological properties includes first normal stress coefficient, first normal stress difference, zero shear viscosity, dynamic viscosity, shear stress, imposed shear rate, and degree of shear thinning.

3. The method of claim 1, wherein the one or more rheological properties is determined using a rheometer.

4. The method of claim 1, wherein the one or more rheological properties is used to calculate at least one of the Weissenberg number and the Deborah number.

5. The method of claim 4, wherein the transport index indicates the relationship between the settling velocity and at least one of the Weissenberg number and the Deborah number.

6. The method of claim 1, wherein the settling velocity is defined as $$V_s = \frac{2a^2}{9\eta(\dot\gamma)}\Delta\rho g - \frac{2a}{3}\frac{\alpha|N_1(\dot\gamma)|}{\eta(\dot\gamma)}.$$

7. The method of claim 1, wherein the settling velocity is defined as $$U = \frac{2a^2\Delta\rho g}{9\eta(\dot\gamma)} - \frac{2}{3}\dot\gamma a\alpha We.$$

8. A method of determining proppant supportability of a carrying fluid including the proppant, the method comprising the acts of:

determining at least one rheological property of the carrying fluid, the at least one rheological property being associated with elasticity or viscosity;

determining the settling velocity of the proppant under imposed shear conditions; and developing a proppant transport index indicating a relationship between the at least one rheological property and the settling velocity, wherein the settling velocity is determined using a flow-through device.

9. The method of claim 8, wherein the at least one rheological property includes first normal stress coefficient, first normal stress difference, zero shear viscosity, dynamic viscosity, shear stress, imposed shear rate, and degree of shear thinning.

10. The method of claim 8, wherein the at least one rheological property is determined using a rheometer.

11. The method of claim 8, wherein the at least one rheological property is used to calculate at least one of the Weissenberg number and the Deborah number.

12. The method of claim 11, wherein the proppant transport index includes a graph of the settling velocity versus at least one of the Weissenberg number and the Deborah number.

13. The method of claim 8, wherein the settling velocity is defined as $$V_s = \frac{2a^2}{9\eta(\dot\gamma)}\Delta\rho g - \frac{2a}{3}\frac{\alpha|N_1(\dot\gamma)|}{\eta(\dot\gamma)}.$$

14. The method of claim 13, wherein the proppant transport index is defined as $$PTI = \frac{V^*}{V_s} = \frac{V^*}{\left[V_0 - \frac{2\dot\gamma a}{3}\alpha We\right]}$$

where $V^* = V_s(\dot\gamma = 0).$

15. The method of claim 8, wherein the settling velocity is defined as $$U = \frac{2a^2\Delta\rho g}{9\eta(\dot\gamma)} - \frac{2}{3}\dot\gamma a\alpha We.$$

16. A method of determining proppant supportability of a carrying fluid including the proppant, the method comprising the acts of:

determining at least one rheological property of the carrying fluid, the at least one rheological property being associated with elasticity or viscosity;

determining the settling velocity of the proppant under imposed shear conditions; and developing a proppant transport index indicating a relationship between the at least one rheological property and the settling velocity, wherein the proppant transport index indicates how much elastic component would be needed to obtain proppant settling at a desired settling velocity and a constant viscosity.

17. A method of determining a transport index of a particle laden fluid, the method comprising the acts of:

determining one or more rheological properties of the fluid at a first shear rate;

determining the settling velocity of the particles at the first shear rate; and obtaining the transport index for the fluid, the transport index indicating a relationship between the settling velocity and the one or more rheological properties, wherein the transport index is defined as $$PTI = \frac{V^*}{V_s} = \frac{V^*}{\left[V_0 - \frac{2\dot\gamma a}{3}\alpha We\right]}$$

where $V^* = V_s(\dot\gamma = 0).$

18. The method of claim 17, wherein the settling velocity is defined as $$V_s = \frac{2a^2}{9\eta(\dot\gamma)}\Delta\rho g - \frac{2a}{3}\frac{\alpha|N_1(\dot\gamma)|}{\eta(\dot\gamma)}.$$

19. The method of claim 17, wherein the settling velocity is determined using a flow-through device.

20. The method of claim 17, wherein the one or more rheological properties is associated with elasticity or viscosity.

\* \* \* \* \*